US00PP35455P2

(12) United States Plant Patent
Hansen

(10) Patent No.: US PP35,455 P2
(45) Date of Patent: Nov. 7, 2023

(54) ***HIBISCUS* PLANT NAMED 'ANGEL EYES'**

(50) Latin Name: ***Hibiscus* hybrid (L.)**
Varietal Denomination: Angel Eyes

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 42 days.

(21) Appl. No.: 17/803,934

(22) Filed: Jan. 26, 2023

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

*Primary Examiner* — Keith O. Robinson

(57) ABSTRACT

A new and distinct cultivar of winter-hardy, herbaceous, perennial, hybrid *Hibiscus* plant named 'Angel Eyes' comprising a rounded mound habit of multiple, well-branched, basal stems producing flowers starting earlier than most cultivars, opening from the bottom to the top of the mound beginning in late July and continuing for at least twelve weeks. Flowers have overlapping petals of near white with shiny deep-red eye and raspberry-red veins projecting into the middle of the petals. The foliage is primarily three-lobed and dark-green-colored. The new plant is useful in the landscape as a specimen or in mass.

2 Drawing Sheets

Botanical classification: *Hibiscus* hybrid (L.).
Variety denomination: 'Angel Eyes'.

STATEMENT REGARDING PRIOR DISCLOSURES UNDER 37 CFR 1.77(b)(6)

The first publically released information of the new plant was on Feb. 1, 2022, when it was displayed with a photograph and brief non-enabling description on the website operated by Walters Gardens, Inc. The first disclosure, in the form of a sale, was made by Walters Gardens, Inc. on May 9, 2022. Walters Gardens, Inc. obtained the new plant and all information relating thereto, from the inventor. No plants of *Hibiscus* 'Angel Eyes' have been sold, in this country or anywhere in the world, by any name, nor has any disclosure of the new plant been made more than one year prior to the filing date of this application, and such sale or disclosure within one year was either derived directly or indirectly from the inventor.

BACKGROUND AND ORIGIN OF THE PLANT

The present invention relates to the new and distinct hardy, herbaceous, *Hibiscus* plant, *Hibiscus* 'Angel Eyes' hybridized under the direction of the inventor on Aug. 8, 2018, at a wholesale perennial nursery in Zeeland, Mich. The new plant is a hybrid of the unreleased, proprietary hybrid known as 16-69-2 (not patented) times the unreleased, proprietary hybrid known as 16-4-1 (not patented). During the trial process, the new plant was assigned the breeder code labeled 18-109-3. Both parents have a complex mixture of species in them, comprising the species: *moscheutos, lasiocarpos*, and *coccineus*.

*Hibiscus* 'Angel Eyes' was first asexually propagated in the late summer of 2020 by sterile shoot-tip tissue culture and later by shoot-tip cuttings at the same nursery in Zeeland, Mich. The resultant asexually propagated plants have found both propagation methods to be stable and true to type in successive generations of asexual reproduction.

BRIEF SUMMARY OF THE PLANT

*Hibiscus* 'Angel Eyes' differs from its parents as well as all other hardy herbaceous *Hibiscus* known to the applicant in many traits. The most similar *Hibiscus* known to the applicant are: 'Ballet Slippers' U.S. Plant Pat. No. 29,896, 'Cherry Choco Latte' U.S. Plant Pat. No. 30,738, 'Crown Jewels' U.S. Plant Pat. No. 11,857, 'Dark Mystery' U.S. Plant Pat. No. 32,036, and 'Mocha Moon' U.S. Plant Pat. No. 27,837.

'Ballet Slippers' has a more upright habit, and the flowers are more ruffled and blushed pink on the margins, with a smaller red eye, and without the red veining. 'Cherry Choco Latte' has a slightly smaller habit, more burgundy-tinted, dark-green, deeply-dissected foliage, the flowers are larger with a folded leading edge, and the veining is a stronger deep magenta with more magenta blush near the petal margin, and more folded. 'Crown Jewels' has a more purplish cast to foliage and a lower spreading habit. 'Dark Mystery' has a slightly larger habit with deep mahogany-colored foliage and the red veining in the petals is less prominent. 'Mocha Moon' has a slightly shorter habit, the tri-lobed foliage is burgundy-colored, and the flowers have more overlapping petals of white with just a blush of pink and reddish veins extending only a short distance from the eye.

The female parent has a more upright and more branched habit with smaller flowers that are more cupped and the foliage was smaller more dissected. The male parent has a red flower with darker leaves.

*Hibiscus* 'Angel Eyes' is a unique hardy herbaceous *Hibiscus* with the following combined traits:

1. Winter-hardy compact perennial with a rounded mounded habit of multiple, well-branched, basal stems;
2. Many rotate flowers with overlapping petals near white with a shiny deep-red eye and raspberry-red veins;
3. Flowering is one of the earliest cultivars, beginning in late July and continuing for at least twelve weeks;
4. Three-lobed foliage of dark-green color.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source, and direction may cause the appearance of minor variations in color.

DETAILED BOTANICAL DESCRIPTION

Figure 1:
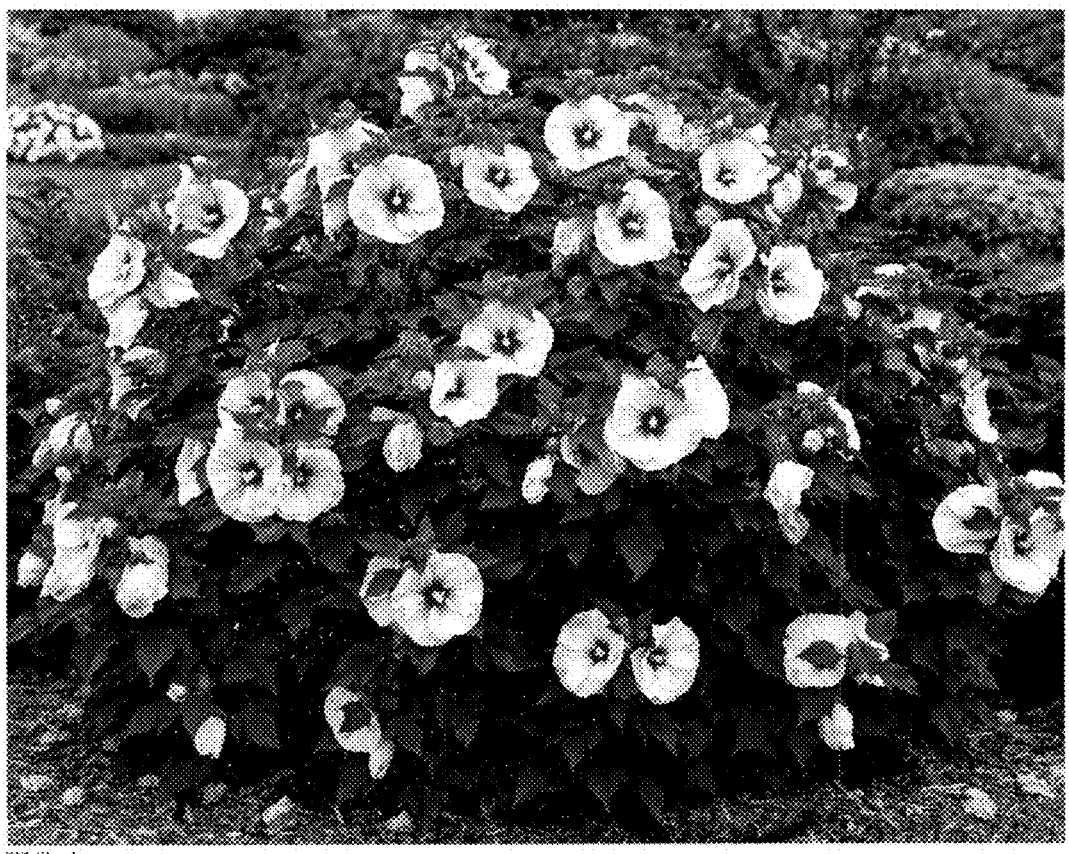
FIG. 1 shows a four-year-old plant in full flower in a display garden.
Figure 2:
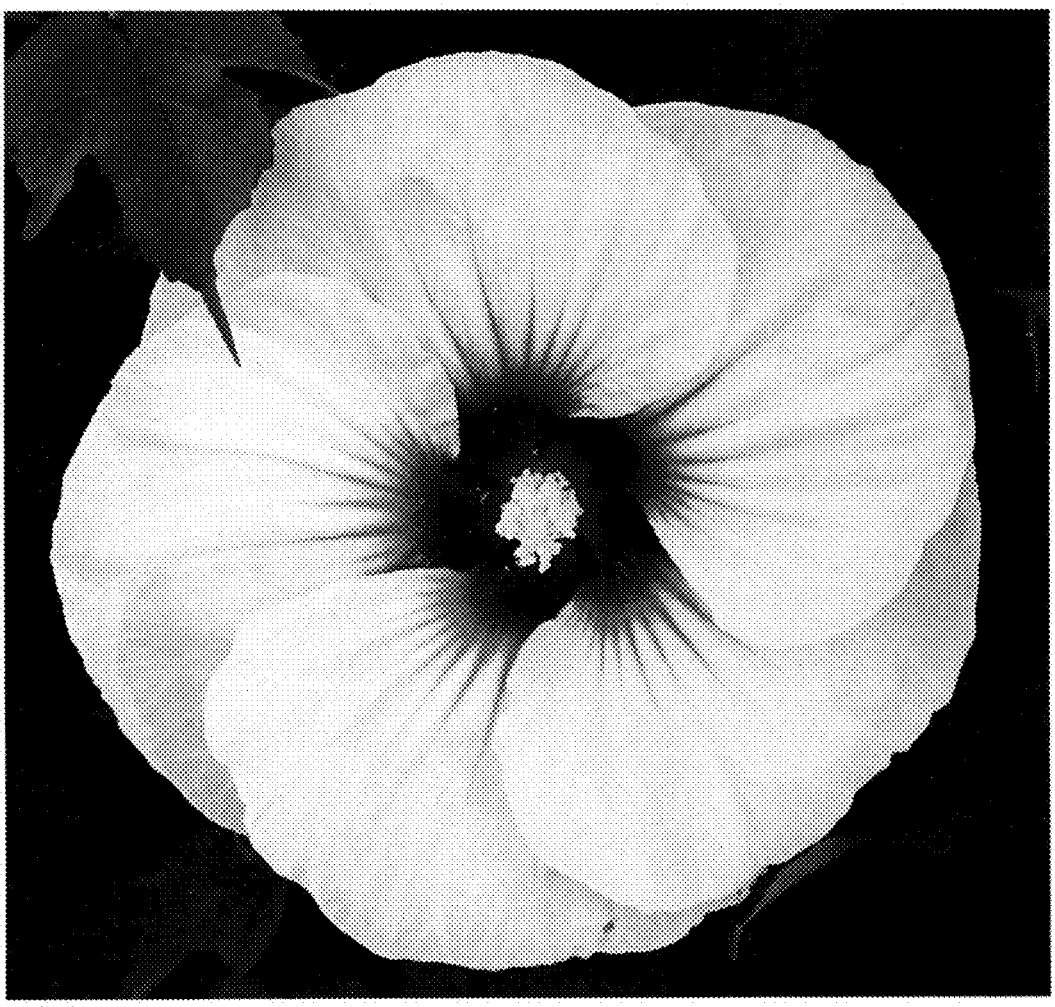
FIG. 2 shows a close-up of the flower and bud.

The following descriptions and color references are based on the 2015 edition of The Royal Horticultural Society Colour Chart except where common dictionary terms are used. The new plant, *Hibiscus* 'Angel Eyes', has not been observed in all possible environments. The phenotype may vary slightly with different environmental conditions, such as temperature, light, fertility, moisture and maturity levels, but without any change in the genotype. The following observations and size descriptions are of three-year-old plants in the loamy-sand, open-field full-sun display garden of a nursery in Zeeland, Mich. with supplemental fertilizer and water as needed. The plants are of natural habit and were not treated with plant growth regulators, nor were they pinched at any time in the growth year.

Parentage: The female or seed parent is the unreleased, non-patented, proprietary *Hibiscus* known by the breeder code 16-69-2, the male or pollen parent is the unreleased, non-patented, proprietary *Hibiscus* known by the breeder code 16-4-1;

Propagation:

*Method*.—Shoot tip cuttings and sterile shoot-tip plant tissue culture division.

*Time to initiate roots from tissue culture*.—About two weeks.

*Rooting habit*.—Normal, branching, developing thick to about 2.2 cm diameter, fleshy; root color creamy yellow nearest RHS 161D depending on soil type.

*Crop time*.—Under normal summer growing conditions 12 to 16 weeks to flower in a four-liter container from cutting. Plant vigor is very good.

Plant description:

*Plant habit*.—Hardy herbaceous perennial with about 60 thick, upright, heavily-branched stems producing an upright spreading mound to about 146 cm tall and about 210 cm wide; flowering in distal one-third of plant with up to about 37 flowers per main stem, average flowers per stem about 30.

*Stem*.—Cylindrical, glabrous, glaucous; to about 145 cm tall and about 23 mm diameter at base, average about 130 cm tall and about 15 mm diameter at base; branched.

*Stem color*.—Proximally between RHS 145A and RHS 148C, distally blend of nearest RHS 146C and RHS 183B.

*Branches*.—To 11 per stem, average about 6 per stem; cylindrical, glabrous, glaucous; to about 22 cm long and 3 mm diameter at base, smaller distally.

*Lateral branch color*.—Nearest RHS 146D in regions without high light exposure and nearest RHS 183B in regions exposed to high light.

*Internode*.—About 18 nodes per stem below branches and 29 below single flowers; average 44 nodes per stem; internode length about 3.0 cm of unpinched plant.

*Internode color*.—Same as surrounding stem.

Foliage description: Predominately tri-lobed with lobes of varying lengths; alternate; coarsely and irregularly dentate; apex and side lobes acute; base cordate; glabrous and matte both abaxial and adaxial; moderately to shallowly incised, with lobes from 1 cm to 5 cm deep;

*Leaf blade size*.—To about 14 cm long and about 12 cm across, average blade size 11 cm long and 10.5 cm wide; no fragrance detected.

*Foliage color*.—Young expanding leaves — adaxial nearest RHS 137A, abaxial nearest RHS 148B; mature leaves — adaxial nearest RHS NN137A, abaxial nearest RHS 147B.

*Veins*.—Palmate; lustrous; costate on abaxial.

*Vein color*.—Adaxial primary veins nearest RHS 187A in basal 15 cm, secondary and distal primary veins nearest RHS 194B; abaxial veins variable, nearest RHS 182C with more light exposure and between RHS 146D and RHS 145C with lower light exposure.

*Petioles*.—Mostly cylindrical, proximally slightly applanate on adaxial side near base; sparsely micro-puberulent; to about 9 cm long and 6 mm across at base, average size about 7 cm long and 4 mm wide at base.

*Petiole color*.—Adaxial variable, nearest RHS 183A to blend of nearest RHS 148A and RHS 176B; abaxial variable, nearest RHS N144D, nearest RHS 146D and a blend between RHS 146D and RHS 176C.

Flower description: Complete; perfect; actinomorphic; rotate; solitary; mostly outward facing; slightly cupped; rotate; lasting up to two days on plant;

Flower size: To about 18.5 cm across and 6 cm deep, decreasing distally; dark red shiny eye medium width, about 4 cm across; smaller later in the season;

*Buds one day prior to anthesis*.—Ellipsoidal with rounded apex and bluntly truncate base; sepals adpressed to petals; to about 5 cm long and about 3.5 cm diameter near middle.

*Bud color one day prior to anthesis*.—Exposed petal color main portion nearest RHS 19D, distal margin nearest RHS 64B, veins with light blush proximally to nearly solid RHS 64A distally, and calyx between RHS 144A and RHS 146B.

*Epicalyx*.—Average about 10 per flower; linear; entire, glabrous, with margin micro-ciliolate; dull surface abaxial and adaxial; sharply acute apex and truncate base, arcuate upwards near apex; to about 31 mm long and about 4 mm wide at base.

*Epicalyx color*.—Adaxial nearest RHS 146B and abaxial nearest RHS 137B with faint blush of nearest RHS 187C.

*Calyx*.—Campanulate, form star-shaped hypanthium; to about 270 mm deep and 54 mm wide at apices.

*Sepals*.—Five; ovate; acute apex; margin entire, edentate; abaxial micro-puberulent and matte, adaxial glabrous and matte; about 32 mm long, about 21 mm wide at fusion, basal 17 mm fused.

*Sepal color*.—Adaxial basal portion nearest RHS 146C, distal portion nearest RHS 147B; abaxial basal portion nearest RHS 146B and distal portion nearest RHS 146B with moderate blush near margins of nearest RHS N187A.

*Inflorescence*.—Up to 38 per main stem and branches without pinching.

*Flower lastingness*.—Persist for one to two days; effective for at least 8 weeks beginning late July.

*Flower fragrance*.—No detectable fragrance.

*Petals*.—Five; glabrous adaxial and abaxial; adaxial eye zone lustrous remaining distal adaxial portion and entire abaxial matte; adnate to the androecium to form a column, imbricate to about 110% overlapping at widest part (petals overlapping both petals on either side, so three petals are stacked about 10%); undulation weak; palmately veined, primary veins slightly impressed on adaxial and slightly costate abaxial; surface mostly flat; apex rounded with distinct basal claw and limb; margins entire, edentate; leading edge not folded under itself.

*Petal size*.—Average about 13 cm across and about 9.2 cm long, claw base about 8 mm across.

*Petal color*.—Adaxial basal 3 mm nearest RHS 59A, distal 15 mm of eye between RHS 187A and RHS N186B, outer portion nearest RHS NN155C with transition zone between eye and outer portion nearest RHS 61B, and veins of nearest RHS 64C in decreasing intensity toward margin; veining longer and prominent with cooler temperatures; abaxial basal 10 mm nearest RHS NN155B, distal 30 mm nearest RHS NN155C, and proximally faintly blushed with nearest RHS 45C, with distal veins variable between RHS 64B and RHS 63D, and proximal veins nearest RHS NN155B.

*Flower lastingness*.—One to two days.

*Gynoecium*.—Single; partially enclosed in column; Column: glabrous and lustrous; about 40 mm long and about 10 mm across at base; with pistil exserted about 17 mm; Column color: nearest RHS NN155C; Style: micro-puberulent in region exserted above column; about 57 mm long, penta-furcate in about distal 7.0 mm, branch diameter about 1 mm; color nearest RHS NN155A in exposed portion, and RHS NN155C portion enclosed in column; Stigma: typically five; flattened globose, puberulent, about 3 mm in diameter and 1.5 mm tall; color in nearest RHS 4D; Ovary: superior; globose, longitudinally grooved in undulated pattern; acute apex, and truncate base; about 11 mm across at base and about 10 mm tall; color nearest RHS N144D.

*Androecium*.—Attached to column; Filaments: numerous, about 100, attached starting about 4 mm from base to 2 mm from apex of column; to about 4 mm long, about 0.2 mm diameter; color nearest RHS N155C; Anthers: flattened reniform; dorsifixed; about 2 mm across, 2 mm long, and about 1 mm thick; color nearest RHS 4D; Pollen: abundant, globose, less than 0.1 mm across; color nearest RHS 158A.

Pedicel: Cylindrical, glabrous in distal portion and micro puberulent in proximal portion; glaucous; length from base of sepal to abscission point about 2 cm long, from abscission point to stem node about 5 cm long; about 3 mm wide; longer on early flowers and decreasing in distal flowers;

Pedicel color: Nearest RHS 146D proximal abscission point, and nearest RHS 146D with moderate blush to nearly solid portions of nearest RHS N187A distal abscission point;

Peduncle: Cylindrical, glabrous, glaucous; flowering portion to about 42 cm tall and about 12 mm diameter at base, average about 35 cm tall and about 10 mm diameter at base;

Peduncle color: Blend of RHS 146C and RHS 183B;

Fruit: Penta-loculicidal capsule; pubescent along inner septa, glabrous outside; ellipsoidal, cuspidate apex and flattened base; about 26 mm long and 22 mm diameter; color nearest RHS 200A when mature; about 85 seeds per fruit;

Seed: Minutely hispidulous; globose; about 3.5 mm in diameter; color between RHS 200C and RHS 200D;

Resistance: *Hibiscus* 'Angel Eyes' has not displayed any pest and disease resistance beyond that typical of hardy perennial *Hibiscus*. The plant grows best with plenty of moisture.

Hardiness at least from USDA zone 4 through 9.

I claim:

1. A new cultivar of hardy herbaceous perennial *Hibiscus* hybrid plant named 'Angel Eyes' as herein illustrated and described.

* * * * *